United States Patent [19]

Sorgenti et al.

[11] 3,949,004

[45] Apr. 6, 1976

[54] HYDROPEROXIDE PRODUCTION

[75] Inventors: Harold A. Sorgenti, Olympia Fields, Ill.; Stephen N. Rudnick, Roxbury, Mass.

[73] Assignee: Atlantic Richfield Company, Los Angeles, Calif.

[22] Filed: Oct. 23, 1973

[21] Appl. No.: 408,957

Related U.S. Application Data

[63] Continuation of Ser. No. 124,971, March 16, 1971, abandoned.

[52] U.S. Cl. ...... 260/610 B; 260/632 C; 260/586 C; 260/631 R
[51] Int. Cl.$^2$ ................. C07C 179/02; C07C 31/13; C07C 45/16
[58] Field of Search ........ 260/610 B, 610 A, 632 C, 260/618 C, 586 C, 124, 632, 632 R, 631 R

[56] References Cited
UNITED STATES PATENTS

| | | | |
|---|---|---|---|
| 2,733,270 | 1/1956 | Fisher | 260/604 |
| 2,843,633 | 7/1958 | Natta | 260/610 B |
| 3,340,304 | 9/1967 | Schulz et al. | 260/586 B |
| 3,564,058 | 2/1971 | Lang | 260/586 B |

FOREIGN PATENTS OR APPLICATIONS

| | | | |
|---|---|---|---|
| 700,546 | 12/1953 | United Kingdom | 260/610 B |

Primary Examiner—James O. Thomas, Jr.
Assistant Examiner—W. B. Lone
Attorney, Agent, or Firm—John C. Martin, Jr.

[57] ABSTRACT

Method for the production of hydroperoxides of hydrocarbon having no aliphatic or cycloaliphatic tertiary carbon atoms, wherein such hydrocarbons are oxidized in the liquid phase with molecular oxygen in the presence of a stabilizing agent. This method gives high hydroperoxide selectivities at high conversion levels.

9 Claims, No Drawings

3,949,004

HYDROPEROXIDE PRODUCTION

RELATED APPLICATIONS

This is a continuation of United States patent application Ser. No. 124,971, filed Mar. 16, 1971, and now abandoned.

BACKGROUND OF THE INVENTION

1. Field of the Invention

This invention relates to the production of hydroperoxides of hydrocarbons having no aliphatic or cycloaliphatic tertiary carbon atoms and more particularly, it relates to the production of the hydroperoxides by oxidation of such hydrocarbons in the liquid phase with molecular oxygen as the oxidizing agent.

2. Prior Art

It is well-known from the published technical and patent literature that the oxidation of hydrocarbons having tertiary carbon atoms such as isobutane, cumene, p-cymene, and the like to the corresponding hydroperoxides using molecular oxygen is commercially feasible. High selectivities at high conversions and conversion rates are readily obtainable.

The oxidation of hydrocarbons which do not have a tertiary carbon atom such as cyclohexane, ethylbenzene and the like to the corresponding hydroperoxide using molecular oxygen is not commercially feasible, since only at very low conversions and conversion rates is it possible to obtain a reasonably high selectivity for the hydroperoxide, i.e. about 50 percent.

These findings are explained by the fact that the tertiary carbon-hydrogen bond is the weakest bond in the compounds containing a tertiary carbon and accordingly, this bond is attacked readily in the oxidation reaction giving a high rate of conversion and producing a tertiary hydroperoxide which is quite stable. This permits the reaction to be carried out to a high conversion level of the hydrocarbon while at the same time the selectivity to the hydroperoxide is very good. Only small amounts of acidic and high boiling residue is produced. This not true for the oxidation of hydrocarbons having no aliphatic or cycloaliphatic tertiary carbon atoms, e.g. those having aliphatic or cycloaliphatic secondary carbon-hydrogen bonds. The rate of conversion is much slower because of the increased bond strength of the secondary carbon-hydrogen bond and the oxidation must be carried out at low conversion of the hydrocarbon to obtain high yields of the hydroperoxide, which moreover, is considerably less stable than the tertiary hydroperoxides. If it is attempted to carry out the oxidation at high conversions large amounts of high boiling residues are produced since competing side reactions occur.

The literature shows, for example, that the total conversion in the oxidation of cyclohexane cannot be above about 1.5 – 2 percent if a 50 percent yield of the hydroperoxide is desired. At a 4 percent conversion the maximum yield of the hydroperoxide is only about 30 percent.

Because of these problems most of the patents relating to the oxidation of cyclohexane, for example, are directed primarily toward improving yields of cyclohexanol, cyclohexanone or adipic acid instead of producing cyclohexyl hydroperoxide. Moreover, most of these patents show the use of heavy metal catalysts which causes rapid decomposition of any cyclohexyl hydroperoxide which might be produced.

The present invention differs from the prior art in that the reaction must be carried out in the absence of any catalytic material and in the presence of a stabilizing agent. Under these conditions of the instant invention there is a high selectivity for the production of the hydroperoxide while the production of the alcohol, ketone and acid is minimized.

SUMMARY OF THE INVENTION

In accordance with this invention hydrocarbons having no aliphatic or cycloaliphatic tertiary carbon atoms such as the cycloalkanes and alkyl substituted aromatics are oxidized with molecular oxygen in the presence of a tertiary alcohol, water or an aqueous buffer solution to produce the corresponding hydroperoxide of the hydrocarbon. The stabilizing agent should not be in excess of about 20 weight percent of the hydrocarbon being oxidized. Temperatures in the range of 80° C. to 180° C. and pressures in the range of from atmospheric to 300 psi. can be employed. Reactions may be carried out either continuously or batchwise, however, in all cases good mixing, i.e. contact, should be employed.

It is an object of this invention therefore, to provide an improved method for the production of hydroperoxides of hydrocarbons having no aliphatic or cycloaliphatic tertiary carbon atoms in the molecule.

It is another object of this invention to provide a method for the production of hydroperoxides of hydrocarbons having no aliphatic or cycloaliphatic tertiary carbon atoms using molecular oxygen, wherein high hydroperoxide selectivities are obtained at high conversion levels.

It is another object of this invention to provide a method for the production of hydroperoxides of hydrocarbons having no aliphatic or cycloaliphatic tertiary carbon atoms using molecular oxygen in the presence of a stabilizing agent.

Other objects of this invention will be apparent from the following description of the preferred embodiments and from the claims.

DESCRIPTION OF THE PREFERRED EMBODIMENTS

The hydrocarbons which are oxidized in accordance with the method of this invention are those having aliphatic primary and secondary carbon atoms and no aliphatic tertiary carbon atoms and those having only cycloaliphatic secondary carbon atoms and and no cycloaliphatic tertiary carbon atoms. Examples of the first group are ethylbenzene, n-propylbenzene, n-butylbenzene, diethylbenzene, di-n-propylbenzene and the like. Aromatic ring carbons are neither aliphatic nor cycloaliphatic and they cannot be oxidized in the manner of either secondary or tertiary aliphatic or cycloaliphatic carbons. Examples having only secondary cycloaliphatic carbon atoms are the cycloalkanes, e.g. cyclopentane, cyclohexane, cycloheptane, cyclooctane, and the like. In general, the invention has its greatest utility for the production of the hydroperoxides of hydrocarbons having from 5 to 12 carbon atoms in the molecule.

The molecular oxygen may be either in the pure form or it may be admixed with the one or more inert gases, for example, $N_2$ and can be in the form of air, the important factor being that the pressure employed provides a sufficiently high concentration of oxygen in the reaction zone to give the desired reaction.

Any tertiary alcohol can be employed as the stabilizing agent, tertiary butyl alcohol being preferred. Other alcohols, such as cumenol, also can be used, also water or an aqueous buffer solution can be employed as the stabilizing agent with the buffer preferably being sodium pyrophosphate or potassium acid phosphate, i.e. either the mono-potassium dihydrogen orthophosphate or the dipotassium monohydrogen orthophosphate. The quantity of the stabilizing agent can range from about 2 to 20 weight percent of the hydrocarbon being oxidized, and preferably range from about 4 to 12 percent by weight. In the case of the buffer solution an aqueous solution of from 1 to 5 weight percent of the salt is satisfactory, although higher concentrations can be employed.

Reaction temperatures in the range of from 80° C. to 180° C. are suitable, a more preferred range being from about 130°C. to 170° C., with a particularly preferred range being from 145° C. to 155° C. Pressures in the range of from atmospheric to 300 psi. can be employed, although pressures from about 100 to 250 psi. are completely satisfactory. Practically, the total pressure should be high enough to insure liquid phase at reaction temperature with the oxygen partial pressure being high enough to insure that sufficient oxygen is dissolved in the reaction mixture to provide the necessary reaction.

It is a particularly important feature of this process that the conversion level should not exceed about 10 mole percent since at higher conversions, in spite of the presence of the stabilizing agent, the production of the by-product alcohols, ketones and acids is no longer minimized, but in fact, is promoted. When the foregoing conditions are met in a catalyst free system, i.e. a system particularly free of heavy metal ions, high selectivities of the hydroperoxide are obtained, which is the desired objective together with a high conversion level not previously shown in the prior art.

The following Examples are provided to illustrate the invention in greater detail.

These runs were conducted at various temperatures and at cyclohexane conversion levels from 1 to 9 percent, both with and without stabilizers. Total pressure, oxygen partial pressure, and mixing were held relatively constant. In all of the runs set forth below the reaction was initiated by 0.1 weight percent tertiary butyl hydroperoxide, although in other runs not included here, wherein no initiator was used, no difference in results could be detected. The runs were carried out in a one liter batch reactor which had been acid washed and sodium pyrophosphate treated to remove any active metals from the system, thus insuring a noncatalytic system and preventing catalytic decomposition of the cyclohexyl hydroperoxide as formed. The cyclohexane, initiator and stabilizer (when used) were charged batchwise to the reactor. Air was fed continuously through a dip tube immersed in the liquid. Nitrogen and excess oxygen from the top of the reactor were saturated primarily with cyclohexane, which was condensed and returned to the bottom of the reactor. The exit gas was depressurized (in these runs from 150 psig.) and passed through an ice-water trap to remove any residual cyclohexane before engering a continuous oxygen analyzer. Air input was adjusted such that the percent oxygen in the tail gas was held between 4 and 10 percent oxygen.

EXAMPLE I

In Runs 1 to 4 of this example a temperature of 142° C. and a pressure of 150 psig. was employed. The reaction time, stabilizers, cyclohexane conversion, and product distribution are shown in Table I.

TABLE I

| Run No. | 1 | 2 | 3 | 4 |
|---|---|---|---|---|
| Stabilizer | None | NaPP[1] | KH$_2$PO$_4$[2] | TBA[3] |
| Time, Hours | 4.0 | 4.5 | 7.0 | 6.0 |
| CH conv.[4] | 1.4 | 1.2 | 3.7 | 1.8 |
| Prod. Dist., wt. % | | | | |
| CHHP[5] | 48.6 | 87.0 | 66.1 | 79.5 |
| CHO[6] | 11.2 | 2.2 | 8.1 | 5.8 |
| CHOH[7] | 15.2 | 6.8 | 12.2 | 6.2 |
| Non-cyclics | 25.0 | 4.0 | 13.7 | 8.5 |

Footnotes:
[1] NaPP is 5 wt. per cent on wt. of cyclohexane of a 2 wt. per cent aqueous solution of sodium pyrophosphate
[2] KH$_2$PO$_4$ is 5 wt. per cent on wt. of cyclohexane of a 2 wt. per cent aqueous solution of potassium dihydrogen ortho-phosphate
[3] TBA is 10 wt. per cent on wt. of cyclohexane of tertiary butyl alcohol
[4] CH conv. is wt. per cent conversion of cyclohexane on wt. of cyclohexane charge
[5] CHHP is cyclohexyl hydroperoxide
[6] CHO is cyclohexanone
[7] CHOH is cyclohexanol These runs show that the use of the stabilizers of this invention markedly increase the cyclohexyl hydroperoxide selectivity and decrease the formation of the cyclohexanol, cyclohexanone, and non-cyclic by-products.

EXAMPLE II

In the runs of this example a temperature of 150° C. and a pressure of 150 psig. was employed. The other variables and product distribution are set forth in Table II.

TABLE II

| Run No. | 5 | 6 | 7 | 8 | 9 | 10 | 11 |
|---|---|---|---|---|---|---|---|
| Stabilizer | None | NaPP[1] | H$_2$O[2] | TBA[3] | None | TBA[3] | TBA[3] |
| Time, Hours | 1.8 | 2.82 | 2.33 | 2.42 | 3.5 | 3.5 | 4.3 |
| CH conv.[4] | 4.1 | 4.1 | 3.7 | 3.8 | 7.0 | 7.4 | 8.8 |
| Prod.Dist.,wt.% | | | | | | | |
| CHHP[5] | 26.6 | 58.4 | 54.2 | 56.1 | 28.2 | 49.1 | 49.8 |
| CHO[6] | 55.1[8] | 31.8[8] | 33.2[8] | 26.7[8] | 13.2 | 8.6 | 11.8 |
| CHOH[7] | | | | | 23.2 | 14.6 | 12.6 |

TABLE II-continued

| Run No. | 5 | 6 | 7 | 8 | 9 | 10 | 11 |
|---|---|---|---|---|---|---|---|
| Non-cyclics[9] | 18.3 | 9.8 | 12.6 | 17.2 | 35.2 | 27.7 | 25.8 |

Footnotes:
[1] NaPP is 5 wt. per cent based on wt. of cyclohexane of a 2 wt. per cent aqueous solution of sodium pyrophosphate
[2] H₂O is 5 wt. per cent on cyclohexane of distilled water
[3] TBA is 10 wt. per cent on cyclohexane of tertiary butyl alcohol
[4] CH conv. is wt. per cent conversion of cyclohexane on wt. of cyclohexane charge
[5] CHHP is cyclohexyl hydroperoxide
[6] CHO is cyclohexanone
[7] CHOH is cyclohexanol
[8] Combined value for cyclohexanone and cyclohexanol
[9] In run 5 there was 8.7 wt. per cent adipic acid, 9.6 other
In run 6 there was 7.1 wt. per cent adipic acid, 2.7 other
In run 7 there was 9.0 wt. per cent adipic acid, 3.6 other
In run 8 there was 8.2 wt. per cent adipic acid, 9.0 other.

These runs demonstrate that a marked improvement in selectivity for the production of the hydroperoxide at conversions up to 10 weight percent of the hydrocarbon can be obtained, by the use of the stabilizing agents of this invention. (In this instance weight percent and mole percent are the same.) In addition, the production of the by-product alcohol, ketone, and acids is correspondingly decreased.

It also will be seen from the foregoing examples that by carrying out the method of this invention in the substantial absence of metal ions, in particular heavy metal ions, which catalyze the decomposition of the hydroperoxide, this oxidation method is non-catalytic with respect to such ions, and accordingly, such method provides a high selectivity for the hydroperoxide product while minimizing the by-product alcohol, ketone, acids and other by-products. The oxidate, accordingly, can be used directly as the oxidizing agent in the epoxidation of olefins in the presence of a molybdenum catalyst. In the epoxidation reaction the hydroperoxide is reduced to the alcohol which can be recovered along with any by-product alcohol originally produced when the hydroperoxide was produced. An additional advantage is that the stabilizing agents needed for the method of this invention are commercially available.

We claim:

1. A method for the production of the hydroperoxides of hydrocarbons having no aliphatic or cycloaliphatic tertiary carbon atoms in the molecule, said hydrocarbons being selected from the group consisting of cycloalkanes having from 5 to 12 carbon atoms in the molecule, ethylbenzene, n-propylbenzene, n-butylbenzene, diethylbenzene and di-n-propylbenzene, which comprises contacting said hydrocarbon in the liquid phase with molecular oxygen at a temperature in the range of from 80°C. to 180°C. in the presence of a stabilizing agent selected from the group consisting of a tertiary butyl alcohol and water, said stabilizing agent being in the range of from about 2 weight percent to 20 weight percent based on said hydrocarbon.

2. A method for the production of the hydroperoxides of hydrocarbons having no aliphatic or cycloaliphatic tertiary carbon atoms in the molecule said hydrocarbons being selected from the group consisting of cycloalkanes having from 5 to 12 carbon atoms in the molecule, ethylbenzene, n-propylbenzene, n-butylbenzene, diethylbenzene and di-n-propylbenzene, which comprises contacting said hydrocarbon in the liquid phase with molecular oxygen at a temperature in the range of from 80°C. to 180°C. in the presence of tertiary butyl alcohol, said alcohol being in the range of from about 2 weight percent to 20 weight percent based on said hydrocarbon.

3. The method according to claim 2, wherein said hydrocarbon is cyclohexane.

4. The method according to claim 2, wherein the temperature is in the range of from about 130°C. to 170°C., and the conversion of said hydrocarbon does not exceed about 10 mole percent.

5. The method according to claim 2, wherein said hydrocarbon is cyclohexane, the temperature is in the range of from 145°C. to 155°C., said alcohol is in an amount ranging between 4 weight percent and 12 weight percent based on said hydrocarbon and the conversion of said cyclohexane does not exceed about 10 mole percent.

6. A method for preparing cyclohexylhydroperoxide comprising contacting cyclohexane in the liquid phase with molecular oxygen at a temperature in the range of from 80°C. to 180°C. in the presence of from about 2 weight percent to 20 weight percent based on said cyclohexane of tertiary butyl alcohol.

7. A method for the oxidation of cyclohexane to produce a mixture of oxidation products comprising cyclohexyl hydroperoxide, cyclohexanol, and cyclohexanone comprising contacting said cyclohexane in the liquid phase with molecular oxygen at a temperature in the range of from 80°C. to 180°C. in the presence of about 2 weight percent to 20 weight percent based on said cyclohexane of tertiary butyl alcohol.

8. The method of claim 7 wherein said cyclohexyl hydroperoxide is subsequently reduced to cyclohexanol.

9. The method of claim 8 wherein cyclohexanol is recovered from the reaction mixture.

* * * * *